US011147992B2

(12) United States Patent
Fisher et al.

(10) Patent No.: US 11,147,992 B2
(45) Date of Patent: *Oct. 19, 2021

(54) LOW WATER STANNOUS FLUORIDE PLUS ZINC CITRATE DENTIFRICE WITH IMPROVED STABILITY, RHEOLOGY, AND EFFICACY

(71) Applicant: Colgate-Palmolive Company, New York, NY (US)

(72) Inventors: Steven Fisher, Middlesex, NJ (US); Linh Fruge, Hillsborough, NJ (US); Michael Prencipe, West Windsor, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/660,851

(22) Filed: Oct. 23, 2019

(65) Prior Publication Data

US 2020/0054900 A1 Feb. 20, 2020

Related U.S. Application Data

(63) Continuation of application No. 15/964,138, filed on Apr. 27, 2018, now Pat. No. 10,682,532, which is a continuation of application No. 13/503,801, filed as application No. PCT/US2009/062452 on Oct. 29, 2009, now Pat. No. 9,968,803.

(51) Int. Cl.
*A61Q 11/00* (2006.01)
*A61K 8/20* (2006.01)
*A61K 8/24* (2006.01)
*A61K 8/365* (2006.01)

(52) U.S. Cl.
CPC .............. *A61Q 11/00* (2013.01); *A61K 8/20* (2013.01); *A61K 8/24* (2013.01); *A61K 8/365* (2013.01); *A61K 2800/31* (2013.01)

(58) Field of Classification Search
CPC .......... A61Q 11/00; A61K 8/24; A61K 8/365; A61K 8/20; A61K 2800/31; A61P 31/04
See application file for complete search history.

(56) References Cited

U.S. PATENT DOCUMENTS

| 2,946,725 | A | 7/1960 | Norris et al. |
| 3,070,510 | A | 12/1962 | Cooley |
| 3,538,230 | A | 11/1970 | Pader et al. |
| 3,678,154 | A | 7/1972 | Widder et al. |
| 3,862,307 | A | 1/1975 | Di Giulio |
| 3,959,458 | A | 5/1976 | Agricola et al. |
| 3,966,863 | A | 6/1976 | Forward et al. |
| 3,980,767 | A | 9/1976 | Chown et al. |
| 4,022,880 | A | 5/1977 | Vinson et al. |
| 4,051,234 | A | 9/1977 | Gieske et al. |
| 4,100,269 | A | 7/1978 | Pader |
| 4,138,477 | A | 2/1979 | Gaffar |
| 4,206,215 | A | 6/1980 | Bailey |
| 4,289,754 | A | 9/1981 | Dhabhar et al. |
| 4,289,755 | A | 9/1981 | Dhabhar |
| 4,325,939 | A | 4/1982 | Shah |
| 4,328,205 | A | 5/1982 | Taylor |
| 4,340,583 | A | 7/1982 | Wason |
| 4,358,437 | A | 11/1982 | Duke |
| 4,416,867 | A | 11/1983 | Ritchey et al. |
| 4,420,312 | A | 12/1983 | Wason |
| 4,421,527 | A | 12/1983 | Wason |
| 4,425,325 | A | 1/1984 | Ritchey et al. |
| 4,568,540 | A | 2/1986 | Asano et al. |
| 4,627,977 | A | 12/1986 | Gaffar et al. |
| 4,647,451 | A | 3/1987 | Piechota, Jr. |
| 4,656,031 | A | 4/1987 | Lane et al. |
| 4,894,220 | A | 1/1990 | Nabi et al. |
| 4,937,066 | A | 6/1990 | Vlock |
| 5,000,944 | A | 3/1991 | Prencipe et al. |
| 5,004,597 | A | 4/1991 | Majeti et al. |
| 5,015,466 | A | 5/1991 | Parran, Jr. et al. |
| 5,240,696 | A | 8/1993 | van Der Ouderaa et al. |
| 5,240,697 | A | 8/1993 | Norfleet et al. |
| 5,288,480 | A | 2/1994 | Gaffar et al. |
| 5,352,439 | A | 10/1994 | Norfleet et al. |
| 5,354,551 | A | 10/1994 | Schmidt |
| 5,372,803 | A | 12/1994 | Williams et al. |
| 5,374,417 | A | 12/1994 | Norfleet et al. |
| 5,486,350 | A | 1/1996 | Norfleet et al. |
| 5,487,906 | A | 1/1996 | Dixit et al. |
| 5,503,823 | A | 4/1996 | Norfleet et al. |
| 5,505,933 | A | 4/1996 | Norfleet et al. |
| 5,546,658 | A | 8/1996 | MacLeod et al. |
| 5,547,658 | A | 8/1996 | Hansenne et al. |
| 5,578,293 | A | 11/1996 | Hansenne et al. |

(Continued)

FOREIGN PATENT DOCUMENTS

| CA | 2330128 | 11/1999 |
| CA | 2441940 | 10/2002 |

(Continued)

OTHER PUBLICATIONS

Brunauer et al., 1938, "Adsorption of gases in multimolecular layers", Journal of the American Chemical Society, 60, 309-319.
Goodson, 1975, "Vitamin E Therapy and Periodontal Disease", Diet Nutrition and Periodontal Disease, pp. 53-66.
Hefferren, 1976, "A Laboratory Method for Assessment of Dentifrice Abrasivity", Journal of Dental Research, 55(4), pp. 563-573.
ISR & Written Opinion for PCT/US06/062499 dated Jun. 22, 2007.
ISR & Written Opinion for PCT/US08/056859 dated Jul. 9, 2008.
ISR & Written Opinion for PCT/US09/062452 dated Aug. 4, 2010.
ISR (Partial) for PCT/US06/062499 dated Apr. 25, 2007.

(Continued)

*Primary Examiner* — Lezah Roberts

(57) ABSTRACT

A dentifrice composition having a low water phase comprising effective amounts of polyphosphate and ionic active ingredients.

8 Claims, 2 Drawing Sheets

(56) References Cited

U.S. PATENT DOCUMENTS

| | | |
|---|---|---|
| 5,578,295 A | 11/1996 | Francis et al. |
| 5,589,160 A | 12/1996 | Rice |
| 5,603,920 A | 2/1997 | Rice |
| 5,651,958 A | 7/1997 | Rice |
| 5,658,553 A | 8/1997 | Rice |
| 5,670,137 A | 9/1997 | Ascione |
| 5,716,600 A | 2/1998 | Zahradnik et al. |
| 5,716,601 A | 2/1998 | Rice |
| 5,718,885 A | 2/1998 | Gingold et al. |
| 5,759,523 A | 6/1998 | Hughes et al. |
| 5,900,230 A | 5/1999 | Cutler |
| 5,939,051 A | 8/1999 | Santalucia et al. |
| 5,939,052 A | 8/1999 | White, Jr. et al. |
| 5,948,390 A | 9/1999 | Nelson et al. |
| 6,019,962 A | 2/2000 | Rabe et al. |
| 6,024,891 A | 2/2000 | Hughes |
| 6,123,950 A | 9/2000 | Hughes |
| 6,139,823 A | 10/2000 | Drechsler et al. |
| 6,162,418 A | 12/2000 | Randive et al. |
| 6,187,293 B1 | 2/2001 | Ballard |
| 6,190,644 B1 | 2/2001 | McClanahan et al. |
| 6,221,340 B1 | 4/2001 | Yu et al. |
| 6,290,933 B1 | 9/2001 | Durga et al. |
| 6,403,059 B1 | 6/2002 | Martin et al. |
| 6,423,300 B1 | 7/2002 | Kleinberg et al. |
| 6,503,484 B2 | 1/2003 | Littlewood et al. |
| 6,592,882 B2 | 7/2003 | George et al. |
| 6,685,920 B2 | 2/2004 | Baig et al. |
| 6,685,921 B2 | 2/2004 | Lawlor |
| 6,696,045 B2 | 2/2004 | Yue et al. |
| 6,861,048 B2 | 3/2005 | Yu et al. |
| 7,063,833 B2 | 6/2006 | Glandoif et al. |
| 7,119,117 B2 | 10/2006 | Beinlich et al. |
| 7,797,403 B2 | 9/2010 | Vedula et al. |
| 8,974,772 B2 | 3/2015 | Fruge et al. |
| 9,968,803 B2 | 5/2018 | Fruge et al. |
| 2003/0077332 A1 | 4/2003 | Godfrey |
| 2003/0158111 A1 | 8/2003 | Bar-Or |
| 2003/0206874 A1 | 11/2003 | Doyle et al. |
| 2004/0101493 A1 | 5/2004 | Scott et al. |
| 2005/0096383 A1 | 5/2005 | Olafsson |
| 2005/0175550 A1 | 8/2005 | Nakano et al. |
| 2006/0062744 A1* | 3/2006 | Lokken ................ A61K 8/34 424/53 |
| 2006/0120975 A1 | 6/2006 | Scherl et al. |
| 2006/0124035 A1 | 6/2006 | Tuzeneau |
| 2006/0134025 A1 | 6/2006 | Trivedi et al. |
| 2007/0014740 A1 | 1/2007 | Miller et al. |
| 2007/0025928 A1 | 2/2007 | Glandorf et al. |
| 2007/0183989 A1 | 8/2007 | Prencipe et al. |
| 2007/0189983 A1 | 8/2007 | Gordon et al. |
| 2007/0237726 A1 | 10/2007 | White et al. |
| 2008/0305168 A1 | 12/2008 | Moon et al. |

FOREIGN PATENT DOCUMENTS

| | | |
|---|---|---|
| CA | 2468606 | 6/2003 |
| CN | 1418086 | 5/2003 |
| CN | 1479607 | 3/2004 |
| CN | 1592605 | 3/2005 |
| CN | 1713886 | 12/2005 |
| CN | 101495085 | 7/2009 |
| EP | 0095871 | 12/1983 |
| EP | 0426213 | 5/1991 |
| EP | 0528468 | 2/1993 |
| EP | 0638307 | 2/1995 |
| EP | 0657160 | 6/1995 |
| EP | 1448159 | 8/2004 |
| EP | 1595537 | 11/2005 |
| JP | S63-008324 | 1/1988 |
| JP | S64-013015 | 1/1989 |
| JP | H05--097668 | 4/1993 |
| JP | H06-065083 | 3/1994 |
| JP | H08-504816 | 5/1996 |
| JP | 2005-112852 | 4/2005 |
| JP | 2005-132768 | 5/2005 |
| KR | 20030068965 | 8/2003 |
| MX | 2008/007468 | 7/2007 |
| RU | 2131720 | 6/1999 |
| WO | 1992/010994 | 7/1992 |
| WO | 1994/014407 | 7/1994 |
| WO | 1994/026258 | 11/1994 |
| WO | 1995/007682 | 3/1995 |
| WO | 1996/017587 | 6/1996 |
| WO | 1998/017270 | 4/1998 |
| WO | 1998/022079 | 5/1998 |
| WO | 2000/061092 | 10/2000 |
| WO | 2001/068046 | 9/2001 |
| WO | 2002/045678 | 6/2002 |
| WO | 2003/015494 | 2/2003 |
| WO | 2003/017963 | 3/2003 |
| WO | 2003/045344 | 6/2003 |
| WO | 2004/045446 | 6/2004 |
| WO | 2004/047784 | 6/2004 |
| WO | 2005/070378 | 8/2005 |
| WO | 2005/092277 | 10/2005 |
| WO | 2006/013081 | 2/2006 |
| WO | 2007/076001 | 7/2007 |
| WO | 2007/076444 | 7/2007 |
| WO | 2008/041055 | 4/2008 |
| WO | 2010/068474 | 6/2010 |

OTHER PUBLICATIONS

Lienau et al., 2002, "Qualitative and Quantitative Analysis of Tocopherols in Toothpastes and Gingival Tissue Employing HPLC NMR and HPLC MS Coupling", Analytical Chemistry, vol. 74, No. 20, pp. 5192-5198.

Loe et al., 1963, "Periodontal Disease in Pregnancy, I. Prevalence and Severity", Acta Odontologica Scand., 21:533-51.

Loe, 1967, "The Gingival Index, the Plaque Index, and The Retention Index Systems", J. Periodontal, 38:610-616.

Otsuki et al., 2005, Database WPI Week 200534, Derwent Publications Ltd., An 2005-326486, JP 2005-112852, Sunstar Chemical Ind. Co. Ltd: Orally Administered Composition.

Panganamala, et al., 1977, "Differential Inhibitory Effects of Vitamin E and Other Antioxidants on Prostaglandin Synthetase, Platelet Aggregation and Lipoxidase", Prostaglandins—Depts. of Physiology, Chemistry & Pathology—The Ohio State University, 14(2), pp. 261-271.

Violi et al., 2004, "Vitamin E for the Treatment of Cardiovascular Disease: Is There a Future?", Annals of New York Academy of Sciences, 1031, pp. 292-304.

WHO, 2005, "What is Health", http://www.bestreferat.ru/refran-2894.html.

Zhou, Guji, 2004, "Introduction to Vitamin E and Its Application in Toothpaste", Toothpaste Industry, vol. 3, p. 25.

\* cited by examiner

LOW WATER STANNOUS FLUORIDE PLUS ZINC CITRATE DENTIFRICE WITH IMPROVED STABILITY, RHEOLOGY, AND EFFICACY

The present embodiments relate to dentifrice compositions. In particular, the present embodiments relate to dentifrice compositions having a low water phase comprising effective amounts of polyphosphate and ionic active ingredients. The ionic active ingredients may include fluoride ions and metal ions such as stannous and zinc ion source.

BACKGROUND

Polyphosphates and ionic active ingredients have been used in dentifrices to promote oral health. Polyphosphates are known anti-tartar agents that help retard calculus formation. Metal ions such as stannous and zinc ions are known to be effective anti-microbial agents. These metal ions provide anti-gingivitis and anti-plaque benefits and may also improve breath and reduce sensitivity. Stannous fluoride has been used in dentistry since the 1950's as a fluoride source to prevent dental caries. Similarly, zinc citrate has been shown to have anti-plaque, anti-gingivitis and anti-tartar efficacy. In addition, zinc has also shown its efficacy as an anti-malodor agent.

While such actives have previously been used in dentifrices, for several reasons it has proven challenging to provide these actives together in a stable single phase. Once such technical problem is to preserve the bioavailability of stannous ions and maximize the chemical stability of the stannous ion source. Certain polyphosphates are unstable in high aqueous systems. Such polyphosphates in an aqueous system are susceptible to hydrolysis unless they are present at a high pH, which is not compatible with high stannous availability. Stannous fluoride tends to precipitate stannous ions in aqueous environments, thereby reducing the efficacy of the stannous ions in the oral care composition. Additionally, the polyphosphates react with ionic fluoride in oral compositions at ambient temperature to produce monofluorophosphate ions and alter the pH of the composition. This reaction compromises the efficacy of the oral composition and its ability to provide stable ionic fluoride and polyphosphate to the oral surfaces.

Other attempts to provide such efficacious dentifrice compositions have reduced the amount of water present in the composition. Reducing the amount of water would theoretically reduce or eliminate the stability issues associated with the fluoride, polyphosphate and other ionic actives. However, reducing the level of water, and optionally replacing some or all of the removed water with a humectant, creates problems in obtaining acceptable rheology and thickening properties in the composition. When water, which is a highly polar solvent, is removed, conventional thickening agents such as carboxymethylcellulose ("CMC") tend to inadequately gel up. Attempts to reduce water content in dentifrice compositions have included the dentifrices described in, e.g., EP 0 638 307 B1; U.S. Pat. Nos. 4,647,451; and 5,670,137. Such known formulations have been shown to exhibit progressive thickening over time, which prolongs the time period or even prevents the dentifrice from reaching a rheological steady state. Ideally, dentifrice formulations need to reach a steady state for consumer acceptance within two weeks. If a formulation routinely increases in viscosity over time, dispensing of the formulation will become difficult, which will likely result in consumer dissatisfaction.

U.S. Pat. No. 6,696,045 discloses dentifrice compositions comprising a single low water phase comprising polyphosphate and ionic active ingredients. Although compositions comprising glass H polyphosphate, which has a long chain of about 21 phosphate groups, and sodium or stannous fluoride are disclosed, with the sodium fluoride being optionally combined with zinc citrate and the stannous fluoride being optionally combined with zinc lactate, there is no disclosure of how to combine stannous, fluoride and zinc salts in a low water composition in combination with short chain length polyphosphates in a low water single phase system.

U.S. Pat. No. 5,578,293 discloses dentifrice compositions comprising a high water phase comprising polyphosphate and ionic active ingredients, including stannous ions.

U.S. Pat. No. 5,487,906 also discloses dentifrice compositions comprising a high water phase comprising polyphosphate and ionic active ingredients, including stannous ions.

Other attempts to provide dentifrice compositions having these actives in efficacious amounts involved the use of dual compartmented packaging wherein the reactive ingredients are physically separated until the time of brushing. (See, e.g., WO98/22079, "Dentifrice Compositions Containing Polyphosphate and Fluoride.") However, such dual-compartmented packages are typically considerably more expensive than the conventional laminate tubes that have been used for many years to contain and dispense dentifrices. They also may be problematic in terms of ease of consumer use and uniform dispensing of approximately equal amounts of each composition during each consumer use. Therefore it remains desirable to provide single phase compositions that can be packaged in conventional laminate squeeze tubes.

The description herein of certain advantages and disadvantages of known compositions, methods, and apparatus is not intended to limit the scope of the embodiments to their exclusion (or inclusion, as the case may be). Indeed, certain embodiments may include one or more known compounds, methods, or apparatus without suffering from the aforementioned disadvantages.

BRIEF SUMMARY

There is a need in the art to provide dentifrice compositions that can effectively combine sources of stannous, fluoride, and zinc ions in combination with a polyphosphate in a low water single phase system that has efficacious delivery of water-unstable actives and/or actives that are reactive with respect to each other in a single phase. There is also a need in the art to provide low water single phase dentifrice compositions that have an improved rheological profile, and in particular have a stable rheology that effectively reduces or eliminates progressive thickening of the composition over time which in turn provides a composition that can effectively be dispensed over the period of its shelf life.

In a first aspect, the embodiments described herein provide a dentifrice composition comprising in a single phase: an orally acceptable vehicle; a source of fluoride ions; a source of stannous ions; a source of zinc ions; and at least one polyphosphate salt selected from the group consisting of inorganic polyphosphate salts that have equal to or less than three phosphorous atoms; wherein the dentifrice composition has a total water content of less than about 10% based on the weight of the composition.

In a second aspect, the embodiments described herein provide a dentifrice composition comprising, in a single phase, an orally acceptable vehicle, the vehicle including a thickening agent comprising a polymer system comprising, in combination, a cross-linked polyvinylpyrrolidone and a gum, wherein the dentifrice composition has a total water content of less than about 10% based on the weight of the composition.

In a third aspect, the embodiments described herein provide a method for the treatment and prevention of bacterial plaque accumulation and/or for the prevention of erosion or demineralization comprising: administering to the oral cavity the dentifrice composition described above.

In a fourth aspect, the embodiments described herein provide a method for the manufacture of a dentifrice composition, the method comprising: providing a source of stannous ions; mixing the source of stannous ions with an aqueous buffer system adapted to chelate the stannous ions in a premix formed thereby; and combining the premix with at least one active component and an orally acceptable vehicle of the dentifrice composition.

As will be demonstrated herein, the preferred embodiments can provide a dentifrice that provides multiple therapeutic benefits by combining stannous ions and fluoride ions, e.g. as stannous fluoride, zinc ions, e.g. as zinc citrate, and polyphosphates, e.g. in the form of tetrasodium pyrophosphate/sodium tripolyphosphate. The use of a particular buffer system can stabilize the stannous ions in the presence of the zinc ions and polyphosphates, and leave the stannous ions active in the single phase low water composition for effective anti-microbial action when used for cleaning the teeth.

The preferred embodiments of the present invention also can provide a dentifrice formulation having a stabilized stannous ion source and a polyphosphate, for example tetrasodium pyrophosphate and/or sodium tripolyphosphate, in a single tube.

The preferred embodiments of the present invention also can provide a low water dentifrice system combining, in a single tube, stannous fluoride, zinc citrate and polyphosphates, in particular having a phosphorous atom of equal to or less than 3, for example tetrasodium pyrophosphate and sodium tripolyphosphate, in a single phase system that provides bioavailable tin, zinc, fluoride and polyphosphate to the oral surfaces.

The preferred embodiments of the present invention also may provide a low water single phase dentifrice system having a stable rheology that does not tend to progressively thicken over time, but instead thickens quickly, for example within a few days of manufacture, and reaches a stable viscosity.

DETAILED DESCRIPTION OF THE EMBODIMENTS

Figure 1:
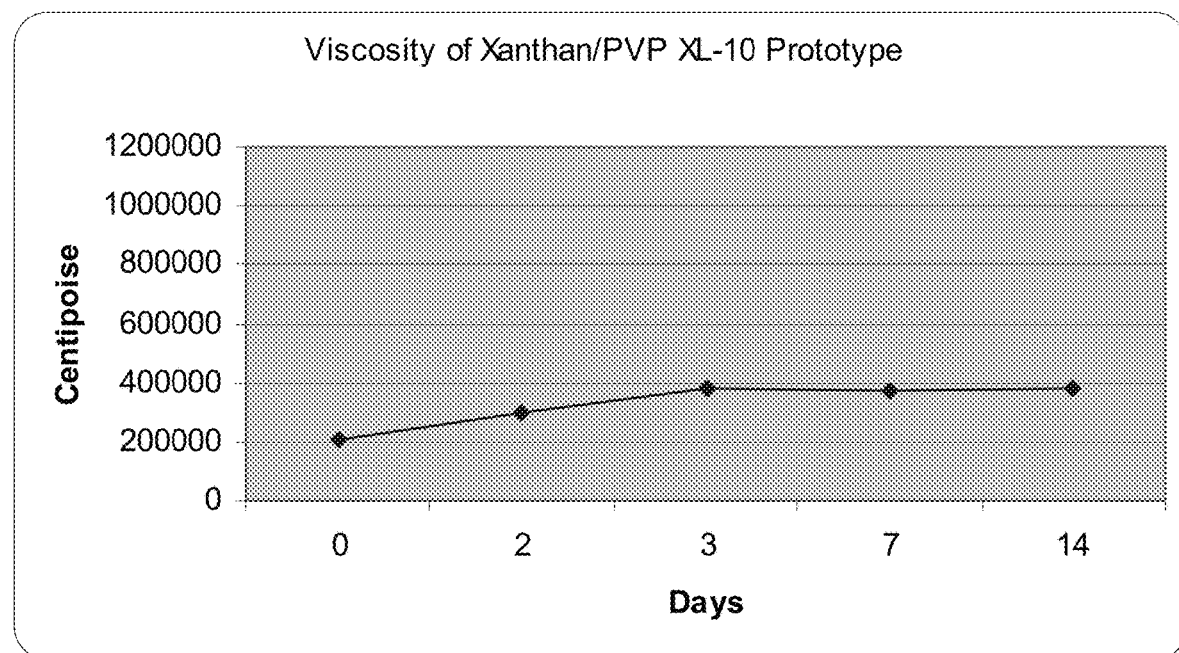
FIG. 1 is a graph showing the relationship between Brookfield viscosity and time (days) for the dentifrice composition of Formula B in the examples.

The following definitions and non-limiting guidelines should be considered in reviewing the description of the invention set forth herein. The headings (such as "Background" and "Summary") and sub-headings used herein are intended only for general organization of topics within the disclosure of the invention, and are not intended to limit the disclosure of the invention or any aspect thereof. In particular, subject matter disclosed in the "Background" may include aspects of technology within the scope of the invention, and may not constitute a recitation of prior art. Subject matter disclosed in the "Summary" is not an exhaustive or complete disclosure of the entire scope of the invention or any embodiments thereof. Classification or discussion of a material within a section of this specification as having a particular utility (e.g., as being an "active" or a "carrier" ingredient) is made for convenience, and no inference should be drawn that the material must necessarily or solely function in accordance with its classification herein when it is used in any given composition.

All publications, patent applications, and issued patents mentioned herein are hereby incorporated in their entirety by reference. The citation of documents herein does not constitute an admission that those documents are prior art or have any relevance to the patentability of the invention disclosed herein. Any discussion of the content of documents cited in the Introduction is intended merely to provide a general summary of assertions made by the authors of the documents, and does not constitute an admission as to the accuracy of the content of such documents.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments also may be preferred, under the same or other circumstances. Furthermore, the recitation of one or more preferred embodiments does not imply that other embodiments are not useful, and is not intended to exclude other embodiments from the scope of the invention.

As used herein, "comprising" encompasses "consisting of" and "consisting essentially of." As used herein, the word "include," and its variants, is intended to be non-limiting, such that recitation of items in a list is not to the exclusion of other like items that may also be useful in the materials, compositions, devices, and methods of this invention.

As used herein, the term "about" when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

All percentages used herein are by weight of the total dentifrice composition, unless otherwise specified. The ratios used herein are weight ratios of the respective components, unless otherwise specified. All measurements are made at 25° C., unless otherwise specified.

As used throughout, ranges are used as a shorthand for describing each and every value that is within the range. Any value within the range can be selected as the terminus of the range.

Herein, "effective amount" means an amount of a compound or composition sufficient to significantly induce a positive benefit, preferably an oral health benefit, but low enough to avoid serious side effects, i.e., to provide a reasonable benefit to risk ratio, within the sound judgment of a skilled artisan.

A dentifrice composition is a product, which in the ordinary course of administration, is not intentionally swallowed for purposes of systemic administration of particular therapeutic agents, but is rather retained in the oral cavity for a time sufficient to contact substantially all of the tooth surfaces and/or oral tissues for purposes of oral activity. A dentifrice composition of the present invention may be in the form of a toothpaste or dentifrice. The term "dentifrice," as used herein, means paste or gel formulations unless otherwise specified. The dentifrice composition may be in any desired form, such as deep striped, surface striped, multi-layered, having the gel surrounding the paste, or any combination thereof.

The phrase "aqueous carrier" as used herein means any safe and effective materials for use in the compositions of the present embodiments. Such materials include thickening agents, humectants, ionic active ingredients, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof.

The embodiments described herein relate to a dentifrice composition having a phase with a low water content and containing an orally acceptable vehicle, a source of fluoride ions, a source of stannous ions, a source of zinc ions, and at least one polyphosphate salt. The polyphosphate salt may be inorganic polyphosphate salts which have three or less phosphorous atoms. The dentifrice composition may have a total water content of less than about 10% based on the weight of the composition. The dentifrice composition preferably has a total water content of less than about 6% based on the weight of the composition.

The vehicle may include a thickening agent comprising a polymer system comprising at least one of a cross-linked polyvinylpyrrolidone and a gum. The thickening agent may comprise, in combination, the cross-linked polyvinylpyrrolidone and the gum. The gum may comprise xanthan gum. The gum may comprise from 0.1 to 0.5 wt % of the composition, preferably from 0.2 to 0.3 wt % of the composition.

The cross-linked polyvinylpyrrolidone may comprise a homopolymer of N-vinyl-2-pyrrolidone. The cross-linked polyvinylpyrrolidone may comprise from 0.05 to 15 wt % of the composition, preferably from 0.75 to 1.25 wt % of the composition.

The at least one polyphosphate may be selected from the group consisting of an alkali metal salt of a pyrophosphate or a tripolyphosphate, preferably the at least one polyphosphate is selected from the group consisting of tetrasodium pyrophosphate or sodium tripolyphosphate. The at least one polyphosphate may comprise a mixture of tetrasodium pyrophosphate and sodium tripolyphosphate, and preferably the mixture of tetrasodium pyrophosphate and sodium tripolyphosphate comprises the tetrasodium pyrophosphate and sodium tripolyphosphate in about a 2:3 weight ratio. The at least one polyphosphate may comprise from 1 to 10 wt % of the composition, preferably from 3 to 7 wt % of the composition.

Preferably, the source of fluoride ions and the source of stannous ions comprise stannous fluoride. Preferably, the source of zinc ions comprises a zinc salt of an organic acid, more preferably zinc citrate. The source of zinc ions may also comprise any zinc compound including, for example, zinc oxide, zinc tartrate, zinc gluconate, and the like.

In the dentifrice composition, the thickening agent may further comprise at least one of a cellulose and a synthetic block copolymer of ethylene oxide and propylene oxide. The composition may further comprise at least one humectant selected from the group consisting of glycerin, polyethylene glycol, propylene glycol, and mixtures thereof.

Preferably, the composition further comprises an aqueous buffer system for the source of stannous ions. The buffer system preferably is adapted to chelate the stannous ions in the composition. The buffer system may comprise at least one of an organic acid or an alkali metal salt thereof, the organic acid preferably being citric acid. The buffer system may comprise a mixture of citric acid and trisodium citrate. The buffer system may comprise from 1 to 5 wt % of the composition. The buffer system may be present, by weight, in an amount that is greater than the amount, by weight, of the source of stannous ions.

The use of the buffer system described herein is believed to reduce or eliminate precipitation of insoluble tin compounds. While not intending on being bound by any theory of operation, the inventors believe that an aqueous buffer system, e.g. a citrate buffer system, which may be employed as a premix for the stannous salt to chelate the stannous ions, can reduce or eliminate the precipitation of insoluble tin compounds in the presence of zinc ions and polyphosphates in a low water dentifrice composition.

Correspondingly, the present invention also provides a method for the manufacture of a dentifrice composition, the method comprising providing a source of stannous ions, mixing the source of stannous ions with an aqueous buffer system adapted to chelate the stannous ions in a premix formed thereby, and combining the premix with at least one active component and an orally acceptable vehicle of the dentifrice composition.

The present invention also provides a dentifrice composition comprising, in a single phase, an orally acceptable vehicle, the vehicle including a thickening agent comprising a polymer system comprising, in combination, a cross-linked polyvinylpyrrolidone and a gum, wherein the dentifrice composition has a total water content of less than about 10% based on the weight of the composition.

While not intending on being bound by any theory of operation, the present inventors believe that a particular thickening system, which employs a cross-linked polyvinylpyrrolidone in combination with a gum, such as xanthan gum, enables a single phase low water dentifrice composition to achieve a viscosity that is substantially constant and that is sufficiently low to permit the dentifrice composition readily to be dispensed over a long shelf life. Without being bound by any theory, it is believed by the present inventors that the combination of the cross-linked polyvinylpyrrolidone with a gum, such as xanthan gum, permits the polyvinylpyrrolidone polymer thickener to be readily hydrated in the low water system, which allows substantially complete initial hydration of the polymer during manufacture of the dentifrice composition. This tends to minimize subsequent hydration of the polymer, which would tend to cause the polymer to be continuously and progressively hydrated over time subsequent to the initial manufacture, which would remove water from other raw material sources in the composition, resulting in progressive thickening.

While the specification concludes with claims particularly pointing out and distinctly claiming the invention, it is believed that the present invention will be better understood from the following description of preferred embodiments.

Polyphosphate Source

The present embodiments may include a polyphosphate source. Polyphosphates are known to help retard calculus formation. However, it is also known that polyphosphates with an average chain length greater than about 4 will also react with ionic fluoride in oral compositions at ambient temperature and produce monofluorophosphate ions, in addition to altering the pH of the composition. This reaction may compromise the efficacy of the oral composition and its ability to provide stable ionic fluoride and polyphosphate to the oral surfaces. It also is known that to have stable polyphosphate, the total water content and pH of the dentifrice composition should be controlled to reduce the hydrolysis of the polyphosphate.

A polyphosphate generally is understood to consist of two or more phosphate molecules arranged primarily in a linear configuration, although some cyclic derivatives may be present. The preferred inorganic polyphosphate salts, which are preferably alkali metal salts, used in the dentifrice compositions of the present invention have no more than three phosphorous atoms, such as a pyrophosphate, for example tetrasodium pyrophosphate, or a polyphosphate, for example sodium tripolyphosphate. These polyphosphates may be used alone or in any combination thereof.

An effective amount of a polyphosphate source may be from about 0.1% to about 30%, preferably from about 1% to about 26%, more preferably from about 4% to about 20%, and most preferably from about 5% to about 13%, by weight of the total dentifrice composition. A typical range is from about 1% to about 10% by weight of the total dentifrice composition, more typically from about 3% to about 7% by weight of the total dentifrice composition.

Aqueous Carriers

In preparing the present compositions, it is desirable to add one or more aqueous carriers to the compositions. Such materials are well known in the art and are readily chosen by one skilled in the art based on the physical and aesthetic properties desired for the compositions being prepared. Aqueous carriers typically comprise from about 40% to about 99%, preferably from about 70% to about 98%, and more preferably from about 90% to about 95%, by weight of the dentifrice composition.

Total Water Content

Water employed in the preparation of commercially suitable oral compositions should preferably be of low ion content and free of organic impurities. In the dentifrice composition, water will generally comprise less than about 10%, and preferably from about 0% to about 6%, by weight of the composition herein. Polyphosphate and actives such as fluoride and stannous are not dissolved in the compositions herein in such low levels of water. However, these ingredients may be dissolved in the present compositions in other low polar solvents, forming non-ionic molecular structures. In either case, the actives remain stable in the compositions during storage. The fluoride ion and the stannous ion if present will be released from their salt forms or non-ionic solution forms when contacted with saliva and/or water at the time of brushing. Thus there is no need to physically separate the polyphosphate-containing portion of the composition from the ionic active-containing portion of the composition, for example by using a dual compartmented package. In addition, fluoride ion from a variety of sources may be used efficaciously in the present composition; there is no preference for the use of sodium monofluorophosphate as the fluoride ion source that is most compatible with the polyphosphate in the composition as previously described in U.S. Pat. No. 6,190,644, "Dentifrice Compositions Containing Polyphosphate and Sodium Monofluorophosphate."

The amounts of water include the free water that is added plus that which is introduced with other materials, such as with silica, surfactant solutions, and/or color solutions.

Binder System

The dentifrice compositions of the present invention preferably incorporate a binder system incorporating a cross-linked polyvinylpyrrolidone in combination with a gum. The binder system may further incorporate at least one additional thickening agent selected from the group consisting of polysaccharides, carbomers, poloxamers, modified celluloses, and mixtures thereof, and at least one humectant. The thickening agent comprises from about 0.05% to about 3%, and preferably from about 0.1% to 1.5%, by weight of the composition. These binder systems provide desirable consistency and gellation to the low water composition. It has previously been known that gelling materials that provide desirable rheology with water and humectant provide generally less satisfactory rheology when the water is not present to activate their gellation binding properties. This is believed to be especially true of glycerin humectant. The binder system may further comprise additional inorganic thickening agents.

Thickening Agent

Polysaccharides, including gums, that are suitable for use herein include carageenans, gellan gum, locust bean gum, xanthan gum, and mixtures thereof. Carageenan is a polysaccharide derived from seaweed and has been known for use as a binder or thickener in toothpastes, see, e.g., U.S. Pat. Nos. 6,187,293 B1 and 6,162,418. There are several types of carageenan that may be distinguished by their seaweed source and/or by their degree of and position of sulfation. Suitable for use in the present invention are kappa carageenans, modified kappa carageenans, iota carageenans, modified iota carageenans, and mixtures thereof. Carageenans suitable for use herein include those commercially available from the FMC Company under the series designation "Viscarin," including but not limited to Viscarin TP 329, Viscarin TP 388, and Viscarin TP 389.

Gellan gum is another polysaccharide that is suitable for use herein. It is a polysaccharide aerobically fermented by pseudomonas elodea. It can also form an acceptable low water matrix when it is present at a level of from about 0.1% to about 3%, preferably from about 0.4% to about 1.8% (w/w).

Locust bean gum and xanthan gum are also suitable polysaccharides for use herein. Locust bean gum or xanthan gum as thickening agents can form a stable and acceptable dentifrice matrix when water level is lower than 10% in the composition.

Poloxamers are also suitable as thickening agents in the low water matrix herein. Poloxamer is a synthetic block copolymer of ethylene oxide and propylene oxide. It is available in several types. Herein, poloxamer 407 is preferable. It can be partly dissolved in water. When temperature is higher than 65° C., it can dissolve in glycerin. POLOXAMER 407® is available, for example, from the BASF CORPORATION, New Jersey, USA.

Carbomers are also suitable as thickening agents in a low water matrix, especially in non-water matrix.

Modified celluloses such as hydroxyethyl cellulose are also good thickening agents in low water matrix. Since the water level is limited in the present compositions, modified hydroxyethyl cellulose with a hydrophobic chain ($C_{12}$-$C_{20}$) are preferred to increase the solubility and hydration of this thickening agent in other low polar solvents, such as glycerin, propylene glycol and PEG.

Humectant

The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, xylitol, and other edible polyhydric alcohols. Preferred are glycerin, polyethylene glycol, polypropylene glycol, and mixtures thereof, especially mixtures thereof. The humectant generally comprises from about 0.1% to 70%, preferably from about 1% to about 60%, and more preferably from about 15% to 55%, by weight of the composition.

The humectant is believed to have a significant impact on the viscosity of the low water matrix. For example, when using polysaccharide as the thickening agent in the composition, the viscosity of the matrix will increase when the level of glycerin or polyethylene glycol increases. On the contrary, the viscosity of matrix will decrease when the level of propylene glycol increases in the composition.

Inorganic Thickening Agents

The binder system may further comprise additional inorganic thickening agents such as colloidal magnesium aluminum silicate or finely divided silica to further improve texture. Additional inorganic thickening agents if present can be used in an amount from about 0.1% to about 15%, more preferably from about 0.1% to about 5%, by weight of the dentifrice composition.

Ionic Active Ingredient

The dentifrice compositions of the present invention preferably comprise an effective amount of an ionic active ingredient selected from the group consisting of a fluoride ion source, a stannous ion source, a zinc ion source, and mixtures thereof.

Fluoride Ion Source

The fluoride ion source herein is a soluble fluoride source capable of providing free fluoride ions. Soluble fluoride ion sources include sodium fluoride, stannous fluoride, indium fluoride, zinc fluoride, and sodium monofluorophosphate. Sodium fluoride and stannous fluoride are the preferred soluble fluoride ion sources. Norris et al., U.S. Pat. No. 2,946,725, issued Jul. 26, 1960, and Widder et al., U.S. Pat. No. 3,678,154 issued Jul. 18, 1972, disclose such fluoride ion sources as well as others.

The fluoride ion source in the present compositions preferably is present as a solid dispersion in the composition during storage, prior to actual brushing usage of the composition by a consumer. The level of water in the present compositions is too low to permit the fluoride source to dissolve in the composition during storage. Thus, there is no obvious interaction between the fluoride ion and the polyphosphate, or silica if present, during storage, providing a stable composition during storage. When the composition is contacted by saliva and/or water at the time of brushing, the fluoride source preferably will be dispersed and the active ion will be delivered to the oral cavity.

The present compositions may contain a soluble fluoride ion source capable of providing from about 50 ppm to about 3500 ppm, and preferably from about 500 ppm to about 3000 ppm of free fluoride ions. To deliver the desired amount of fluoride ions, fluoride ion source may be present in the total dentifrice composition at an amount of from about 0.1% to about 5%, preferably from about 0.2% to about 1%, and more preferably from about 0.3 to about 0.6%, by weight of the total dentifrice composition.

Metal Ion Source

The present invention may comprise a metal ion source that provides stannous ions, zinc ions, or mixtures thereof. The metal ion source can be a soluble or a sparingly soluble compound of stannous or zinc with inorganic or organic counter ions. Examples include the fluoride, chloride, chlorofluoride, acetate, hexafluorozirconate, sulfate, tartrate, gluconate, citrate, malate, glycinate, pyrophosphate, metaphosphate, oxalate, phosphate, carbonate salts and oxides of stannous and zinc.

Stannous and zinc ions have been found to help in the reduction of gingivitis, plaque, sensitivity, and improved breath benefits. The efficacy of these metal ions in the present compositions is not reduced by the polyphosphate.

Stannous and zinc ions are derived from the metal ion source(s) found in the dentifrice composition in an effective amount. An effective amount is defined as from at least about 1000 ppm metal ion, preferably about 2,000 ppm to about 15,000 ppm. More preferably, metal ions are present in an amount from about 3,000 ppm to about 13,000 ppm and even more preferably from about 4,000 ppm to about 10,000 ppm. This is the total amount of metal ions (stannous and zinc and mixtures thereof) that is present in the compositions for delivery to the tooth surface.

The metal ion sources in the present compositions are preferably not fully ionized in the composition during storage, prior to actual brushing usage of the composition by a consumer. The level of water in the present compositions is too low to permit the metal ion source to dissolve in the composition during storage. But certain salts such as stannous chloride and stannous fluoride, can be solubilized in glycerin or propylene glycol. Both humectants can provide super stability protection for such stannous salts and also can provide a better taste profile than a water (aqueous) solution of stannous. When the composition is contacted by saliva and/or water at the time of brushing, the stannous ion source will be fully ionized and the active ion will be delivered to the oral cavity.

Dentifrices containing stannous salts, particularly stannous fluoride and stannous chloride, are described in U.S. Pat. No. 5,004,597 to Majeti et al. Other descriptions of stannous salt dentifrices are found in U.S. Pat. No. 5,578,293. The preferred stannous salts are stannous fluoride and stannous chloride dihydrate. Other suitable stannous salts include stannous acetate, stannous tartrate and sodium stannous citrate. Examples of suitable zinc ion sources are zinc oxide, zinc sulfate, zinc chloride, zinc citrate, zinc lactate, zinc gluconate, zinc malate, zinc tartrate, zinc carbonate, zinc phosphate, and other salts listed in U.S. Pat. No. 4,022,880.

The combined metal ion source(s) will be present in an amount of from about 0.25% to about 11%, by weight of the final composition. Preferably, the metal ion sources are present in an amount of from about 0.4 to about 7%, more preferably from about 0.45% to about 5%.

Buffering Agent

The compositions described herein also may contain a buffering agent in addition to the chelating buffer agent for the stannous ions that is used in a premix as described hereinabove. Buffering agents, as used herein, refer to agents that can be used to adjust the pH of the compositions to a range of about pH 3.0 to about pH 10. The phase of the dentifrice containing stannous will typically have a slurry pH of from about 3.0 to about 5.5, preferably from about 3.25 to about 5, and more preferably from about 3.4 to about 4.5. The phase of the dentifrice containing the polyphosphate will typically have a slurry pH of from about 4.0 to about 10, preferably from about 4.5 to about 8, and more preferably from about 5.0 to about 7.0. A dentifrice containing both stannous and polyphosphate in a single phase will typically have a pH of from about 4 to about 7, preferably from about 4.5 to about 6, and more preferably from about 5 to about 5.5.

The buffering agents include alkali metal hydroxides, ammonium hydroxide, organic ammonium compounds, carbonates, sesquicarbonates, borates, silicates, phosphates, imidazole, and mixtures thereof. Specific buffering agents include monosodium phosphate, trisodium phosphate, sodium benzoate, benzoic acid, sodium hydroxide, potassium hydroxide, alkali metal carbonate salts, sodium carbonate, imidazole, pyrophosphate salts, citric acid, and sodium citrate. Buffering agents are used at a level of from about 0.1% to about 30%, preferably from about 0.1% to about 10%, and more preferably from about 0.3% to about 3%, by weight of the present composition. When stannous is present in the composition, preferred buffers are sodium hydroxide, potassium hydroxide, and ammonium hydroxide.

Anticalculus Agents

The compositions described herein also may employ, as anticalculus agents, polyphosphate materials known to be effective in reducing calcium phosphate mineral deposition related to calculus formation. Agents included are pyrophosphates, and tripolyphosphates. The compositions may also employ synthetic anionic polymers [including polyacrylates and copolymers of maleic anhydride or acid and methyl vinyl ether (e.g., GANTREZ®), as described, for example, in U.S. Pat. No. 4,627,977 to Gaffar et al.; as well as, e.g., polyamino propane sulfonic acid (AMPS)], zinc citrate trihydrate, diphosphonates (e.g., EHDP; AHP), polypeptides (such as polyaspartic and polyglutamic acids), and mixtures thereof.

Abrasive Polishing Materials

An abrasive polishing material may also be included in the toothpaste compositions. The abrasive polishing material contemplated for use in the compositions of the present invention can be any material that does not excessively abrade dentin. Typical abrasive polishing materials include silicas including gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962. Mixtures of abrasives may also be, used. If the dentifrice composition or particular phase comprises a polyphosphate having an average chain length of about 4 or more, calcium containing abrasives and alumina are not preferred abrasives. The most preferred abrasive is silica.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Preferred are the silica xerogels marketed under the trade name "SYLOID®" by the W. R. Grace & Company, Davison Chemical Division. Also preferred are the precipitated silica materials such as those marketed by the J. M. Huber Corporation under the trade name, "ZEODENT®", particularly the silica carrying the designation "Zeodent 119." The types of silica dental abrasives useful in the toothpastes of the present invention are described in more detail in Wason, U.S. Pat. No. 4,340,583, issued Jul. 29, 1982. Silica abrasives are also described in Rice, U.S. Pat. Nos. 5,589,160; 5,603,920; 5,651,958; 5,658,553; and 5,716,601. The abrasive in the toothpaste compositions described herein is generally present at a level of from about 6% to about 70% by weight of the composition. Preferably, toothpastes contain from about 10% to about 50% of abrasive, by weight of the dentifrice composition.

Peroxide Source

The present invention may include a peroxide source in the composition. The peroxide source is selected from the group consisting of hydrogen peroxide, calcium peroxide, urea peroxide, and mixtures thereof. The preferred peroxide source is calcium peroxide. The following amounts represent the amount of peroxide raw material, although the peroxide source may contain ingredients other than the peroxide raw material. The present composition may contain from about 0.01% to about 10%, preferably from about 0.1% to about 5%, more preferably from about 0.2% to about 3%, and most preferably from about 0.3% to about 0.8% of a peroxide source, by weight of the dentifrice composition.

Alkali Metal Bicarbonate Salt

The compositions also may include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The alkali metal bicarbonate salt also functions as a buffering agent. The present composition may contain from about 0.5% to about 50%, preferably from about 0.5% to about 30%, more preferably from about 2% to about 20%, and most preferably from about 5% to about 18% of an alkali metal bicarbonate salt, by weight of the dentifrice composition.

Additional Aqueous Carriers

The compositions also may comprise surfactants, also commonly referred to as sudsing agents. Suitable surfactants are those that are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976.

Nonionic surfactants that can be used in the compositions can broadly be defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name PLURONIC®), polyoxyethylene, polyoxyethylene sorbitan esters (sold under trade name TWEENS®), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al. in U.S. Pat. No. 4,051,234. The present composition typically comprises one or more surfactants each at a level of from about 0.25% to about 12%, preferably from about 0.5% to about 8%, and most preferably from about 1% to about 6%, by weight of the composition.

Titanium dioxide may also be added to the present composition. Titanium dioxide is a white powder which adds opacity to the compositions. Titanium dioxide generally comprises from about 0.25% to about 5%, by weight of the composition.

Coloring agents may also be added to the present composition. The coloring agent may be in the form of an aqueous solution, preferably 1% coloring agent in a solution of water. Color solutions generally comprise from about 0.01% to about 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the paramenthan carboxyamide agents such as N-ethyl-p-menthan-3-carboxamide (known commercially as "WS-3") and mixtures thereof. A flavor system is generally used in the compositions at levels of from about 0.001% to about 5%, by weight of the composition.

Sweetening agents can be added to the compositions. These include saccharin, dextrose, sucrose, lactose, xylitol, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in toothpastes at levels of from about 0.005% to about 5%, by weight of the composition.

The present invention may also include other agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides, polyphenols, and herbals. The water soluble antimicrobials include quaternary ammonium salts and bis-biquanide salts, among others. Triclosan monophosphate is a preferred additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis[4-(R-amino)-1-pyridinium] alkanes as disclosed in U.S. Pat. No. 4,206,215, issued Jun. 3, 1980, to Bailey.

Other antimicrobials such as copper bisglycinate, copper glycinate, zinc citrate, and zinc lactate may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al. Specific antimicrobial agents include chlorhexidine, triclosan, triclosan monophosphate, and flavor oils such as thymol. Triclosan is a preferred antimicrobial agent for inclusion in the present compositions. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al. The water insoluble antimicrobial agents, water soluble agents, and enzymes may be present in either the first or second dentifrice compositions. The quaternary ammonium agents, stannous salts, and substituted guanidines are preferably present in the second dentifrice composition. These agents may be present at levels of from about 0.01% to about 1.5%, by weight of the dentifrice composition.

A herbal agent, including but not limited to, golden thread extract, honeysuckle extract, and mixtures thereof, may also be present in the compositions herein at levels of from about 0.01% to about 0.05%. Such herbal agents are believed to provide anti-bacterial efficacy. Polyphenols may further be included at levels from about 0.01% to about 2%. A preferred polyphenol is tea polyphenol.

An effective amount of a desensitizing agent may also be incorporated into the present compositions. The desensitizing agents include those selected from alkaline metal salts with a chloride, nitrate sulfate, or acetate of a group II metal or aluminum or polymerizable monomer to occlude the tubules, alkaline metal or ammonium nitrate, ammonium oxylate, citric acid and sodium citrate. Preferred salts are potassium nitrate, potassium citrate, and mixtures thereof. Such desensitizing agents are disclosed in e.g., U.S. Pat. No. 5,718,885.

For compositions that contain stannous, a stain reducing agent such as Plasdone S-630 or aluminum hydrate may further be added to the composition. Plasdone is polyvinyl pyrrolidone (PVP) that can be synthesized by polymerizing vinylpyrrolidone. Commercially, it has been produced as a series of products having mean molecular weights ranging from 10,000 to 700,000. Herein, the low molecular weights and middle molecular weights (from about 10,000 to about 100,000) are preferred. In order to remove stain effectively, the level of PVP is preferably from about 0.5% to about 10%, more preferably from about 1.0% to about 7.0%, and even more preferably from about 1.5% to about 5.0%.

The dentifrice compositions may be a paste, gel, or any configuration or combination thereof. A further embodiment of the present invention includes dual-phase or multi-phase compositions comprising the present low-water compositions as one phase and at least one other separate phase comprising additional dentifrice components to further enhance stability, performance and/or aesthetics of the dentifrice product. For example, a dual phase composition may comprise a first phase comprising the present low-water composition with polyphosphate and ionic active(s) and a separate second phase comprising additional active agents such as bleaching agents, preferably a peroxide source, or a tooth surface conditioning agent to provide improved cleaning, whitening, anti-staining and mouth feel benefits. Examples of tooth conditioning agents are polysiloxanes and modified polysiloxanes, including diorganopolysiloxanes such as polydimethylsiloxane (PDMS); alkyl- and alkoxy-dimethicone copolyols such as $C_{12}$ to $C_{20}$ alkyl dimethicone copolyols; and aminoalkylsilicones. These siloxane polymers are described for example in U.S. Pat. Nos. 5,759,523; 6,024,891; 6,123,950; 6,019,962; 6,139,823 all assigned to The Procter & Gamble Company.

The dispenser for the dentifrice compositions may be a tube, pump, or any other container suitable for dispensing toothpaste. In a dual phase oral composition, each oral composition will be contained in a physically separated compartment of a dispenser and dispensed side-by-side.

Methods of Use

In practicing the embodiments, the user need only apply the dentifrice composition herein, to the tooth surfaces of a human or animal, in the areas desired, in order to obtain a desired effect, e.g., whitening, breath freshening, caries prevention, pain relief, gum health, tartar control, erosion control, etc. Use of dentifrices to control erosion of the tooth surface, or to prevent demineralization, are known and described in, for example, U.S. Pat. No. 6,685,920, the disclosure of which is incorporated by reference herein in its entirety. The compositions also may be applied to other oral cavity surfaces, such as the gingival or mucosal tissues, although it is believed that the benefits are best achieved when the dentifrice compositions are applied to the teeth. The dentifrice composition may contact the tooth and/or oral cavity surface either directly, or indirectly, however, it is preferred that the dentifrice composition be directly applied. The dentifrice composition may be applied by any means, but is preferably applied with a brush or by rinsing with a dentifrice slurry.

The manufacture of the oral composition of the present invention may be accomplished by any of the various standard techniques for producing such compositions. To make a dentifrice, a vehicle may be prepared containing humectant, for example, one or more of glycerin, glycerol, sorbitol, and propylene glycol, thickener agents and anti-bacterial agent such as triclosan, and the vehicle and a mixture of anionic and amphoteric surfactants are added, followed by blending in of a polishing agent, as well as fluoride salts, with the pre-mix. Finally, flavoring agent, is admixed and the pH is adjusted to between 6.8 to 7.0.

The following examples are further illustrative of the preferred embodiments, but it is understood that the invention is not limited thereto.

Example 1

Dentifrice compositions were prepared having the formulations as indicated in Table 1.

TABLE 1

| INGREDIENT | Formula A | Formula B | Formula C | Formula D |
|---|---|---|---|---|
| Deionized water | 6.000 | 6.000 | 4.000 | 4.000 |
| Citric acid | 0.600 | 0.160 | 0.000 | 0.000 |
| Trisodium citrate | 3.000 | 0.810 | 0.000 | 0.000 |
| Zinc citrate | 2.000 | 2.000 | 2.000 | 2.000 |
| Glycerin | 7.700 | 20.000 | 7.700 | 14.000 |
| Stannous fluoride | 0.454 | 0.454 | 0.454 | 0.454 |
| Propylene glycol | 7.000 | 0.000 | 7.000 | 7.000 |
| Polyethylene glycol 600 | 5.000 | 7.000 | 5.000 | 9.000 |
| Tetrasodium pyrophosphate | 2.000 | 2.000 | 2.000 | 2.000 |
| Glycerin | 28.846 | 29.786 | 32.446 | 30.846 |
| Sodium tripolyphosphate | 3.000 | 3.000 | 3.000 | 3.000 |
| Sodium CMC 7MF | 0.700 | 0.000 | 0.700 | 0.700 |
| Sodium CMC 2000S | 1.000 | 0.000 | 1.000 | 0.300 |
| Xanthan gum NF | 0.000 | 0.250 | 0.000 | 0.000 |
| Polyplasdone XL-10 | 0.000 | 1.000 | 0.000 | 0.000 |
| Poloxamer 407 | 1.000 | 0.000 | 1.000 | 0.000 |
| FD&C blue #1 | 0.000 | 0.190 | 0.000 | 0.000 |
| Sodium saccharin | 0.500 | 0.500 | 0.500 | 0.500 |
| Titanium dioxide | 0.500 | 0.150 | 0.500 | 0.500 |
| Zeodent 115 | 12.000 | 12.000 | 12.000 | 10.000 |
| Zeodent 165 | 4.000 | 0.000 | 6.000 | 3.000 |
| Zeodent 105 | 12.000 | 12.000 | 12.000 | 10.000 |
| STP dental cream flavor | 1.200 | 1.200 | 1.200 | 1.200 |
| Sodium lauryl sulfate | 1.500 | 1.500 | 1.500 | 1.500 |
| TOTAL | 100.00 | 100.00 | 100.00 | 100.00 |

Each of the formulations contain 0.454 wt % stannous fluoride, 2 wt % zinc citrate and a polyphosphate anti-tartar control system, comprising 2 wt % tetrasodium pyrophosphate and 3 wt % sodium tripolyphosphate (i.e. tetrasodium pyrophosphate and sodium tripolyphosphate in a 2:3 weight ratio).

The compositions in accordance with Formula A and Formula B incorporated a citrate buffer system comprising a mixture of citric acid and an alkali metal citrate, in particular trisodium citrate. Formula A and Formula B were prepared initially as a premix by dissolving the stannous fluoride in an aqueous solution of citric acid and sodium citrate. The citrate ions in the premix chelate the stannous ion thereby preventing or inhibiting precipitation of the stannous salt in the final composition and reducing the chance of forming insoluble inactive tin compounds in the dentifrice composition. The premix was then mixed with the remaining active constituents and the vehicle of the dentifrice composition.

Example 2

The dentifrice compositions in accordance with Formula A and Formula C were subjected to an accelerated aging study to determine the stability of the stannous salt. The dentifrice compositions were subjected to a temperature of 105° F. for a period of 4 weeks. The initial and final amounts of soluble tin, representing the available stannous ion, were measured at the beginning and at the end of the test. The results are shown in Table 2.

TABLE 2

|  | Formula A | Formula C |
|---|---|---|
| Initial soluble tin (wt %) | 0.33 | 0.24 |
| Final soluble tin (wt %) after 4 weeks at 105° F. | 0.31 | 0.16 |

Table 2 shows that for the composition of Formula A the initial amount of soluble tin was 0.33 wt % which was reduced to 0.31 wt % at the end of the test, this being a small reduction (about 7%) in stannous tin availability which is acceptable in a commercial dentifrice.

Table 2 also shows that for the composition of Formula C the initial amount of soluble tin was 0.24 wt % which was reduced to 0.16 wt % at the end of the test, this being a large reduction (33%) in stannous tin availability which would not be preferred in a commercial dentifrice.

The citrate buffer system in Formula A accordingly stabilizes the stannous ions when in the presence of zinc ions.

Example 3

The aging study discussed above also investigated the stability of other actives in the composition of Formulas A and C, and the results are shown in Table 3.

TABLE 3

|  | Ionic Fluoride (ppm) | Na tripoly Phosphate (wt %) | Na pyro Phosphate (wt %) | Na ortho Phosphate (wt %) | Soluble tin (wt %) | Soluble zinc (wt %) |
|---|---|---|---|---|---|---|
| Formula A | | | | | | |
| Initial | 985 | 2.59 | 2.34 | 0.14 | 0.36 | 0.39 |
| After 4 weeks at 105° F. | 938 | 2.44 | 2.1 | 0.33 | 0.33 | 0.39 |
| After 8 weeks at 105° F. | 1038 | 2.49 | 2.16 | 0.39 | 0.33 | 0.39 |
| After 12 weeks at 105° F. | 950 | 2.26 | 2.11 | 0.45 | 0.35 | 0.34 |
| Formula C | | | | | | |
| Initial | 1029 | 2.86 | 2.07 | none | 0.24 | 0.46 |
| After 4 weeks at 105° F. | 1008 | 2.82 | 1.80 | 0.19 | 0.16 | 0.42 |
| After 8 weeks at 105° F. | 1085 | 2.99 | 2.24 | 0.31 | 0.15 | 0.40 |
| After 12 weeks at 105° F. | 928 | 2.75 | 2.13 | 0.22 | 0.14 | 0.45 |

Although the soluble tin reduced significantly after 4 weeks for Formula C, as discussed above, the soluble tin content did not significantly reduce further up to 12 weeks. The amounts of ionic fluoride, sodium tripolyphosphate, sodium pyrophosphate (which progressively converts into sodium orthophosphate) and soluble zinc remained at acceptable levels after the 12 week accelerated aging test for both Formula A and C.

Example 4

The composition of Formula C was subjected to an in vitro antibacterial test in an artificial mouth to measure the antibacterial efficacy of the formulation which comprised the stannous salt and the zinc salt. The antibacterial efficacy of the formulation was comparable to a commercial dentifrice containing 0.3% Triclosan as an antibacterial component.

Example 5

The formulation of Formula B contained a mixture of a cross-linked polyvinylpyrrolidone and a gum, in particular xanthan gum. More particularly the composition included 1 wt % Polyplasdone XL-10 and 0.25 wt % xanthan gum.

The formulation was subjected to a rheology test to determine any change in viscosity, resulting from progressive thickening, over time. In particular, the composition was subjected to a measurement of Brookfield viscosity. The viscosities of the composition was determined with a Brookfield Viscometer Model RVT or RVTDV attached to a Brookfield Helipath Stand utilizing a RV T-Bar Spindle Set. Viscosity profiles were recorded on a linear 1200 recorder. (Brookfield Engineering Laboratories, Stoughton, Ma.) Brookfield viscosity of the composition was taken at ambient conditions over a period of 14 days and the results are shown in FIG. 1. It may be seen that although the Brookfield viscosity increased substantially (by about 75%) from the initial value over the period of the test, an acceptable viscosity was maintained over the period of the test, with the viscosity reaching an acceptable steady state value after only a few days. The product would be readily dispensable from a container over the expected shelf life of the dentifrice composition.

Figure 2:
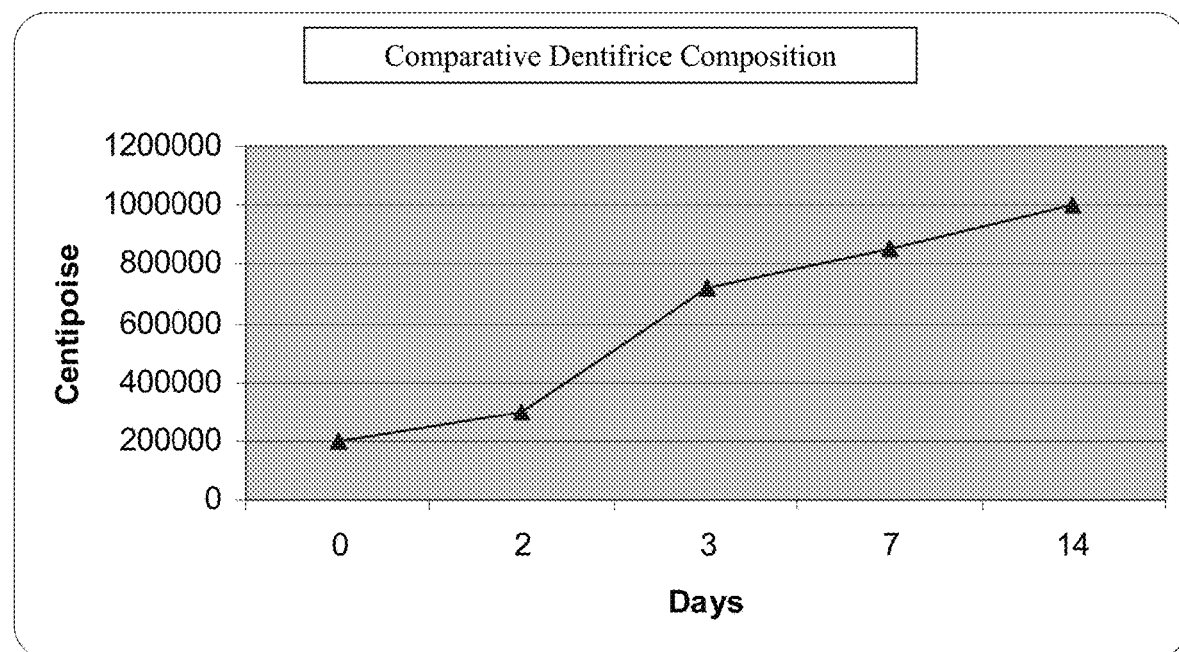
FIG. 2 is a graph showing the relationship between Brookfield viscosity and time (days) for a comparative dentifrice composition.

The Brookfield viscosity of a comparative composition comprising a mixture of carboxymethyl cellulose (CMC) as a thickener and a cross-linked polyvinylpyrrolidone was measured. Specifically, the CMC was 0.7 wt % CMC 7MF and 0.8 wt % CMC 2000S and the cross-linked polyvinylpyrrolidone was 1 wt % Polyplasdone XL-10. All other ingredients were the same as for Formula B. The composition was subjected to the same rheology test over a period of 14 days and the results are shown in FIG. 2. It may be seen that the Brookfield viscosity increased substantially (by about 400%) over the period of the test. This product suffered from the problem of progressive thickening, with the viscosity rapidly becoming too high for easy dispensing of the dentifrice composition from a container. The viscosity did not reach a steady state during the test.

It may be seen therefore that the thickening composition employed in accordance with the preferred embodiments of the present invention enabled a rheological steady state to be reached and for any progressive thickening of the dentifrice composition to be reduced or eliminated.

We claim:
1. A dentifrice composition comprising:
 a coloring agent;
 a crosslinked polyvinyl pyrrolidone;
 at least one humectant; and
 an orally acceptable vehicle, wherein the vehicle comprises a thickening agent comprising, in combination, a cross-linked polyvinylpyrrolidone present in an amount of about 0.75 to 1.25 wt % of the composition and xanthan gum present in an amount from about 0.2 to 0.3 wt % of the composition;

wherein the composition comprises water; and wherein the dentifrice composition has a total water content of less than about 10% based on the weight of the composition.

2. The dentifrice composition of claim 1, wherein the coloring agent is FD&C Blue#1.

3. The dentifrice composition of claim 1, wherein the total water content is of less than about 6% based on the weight of the composition.

4. The dentifrice composition of claim 1, wherein the humectant is selected from the group consisting of glycerin, glycerol, polyethylene glycol, sorbitol propylene glycol.

5. The dentifrice composition of claim 1, wherein the humectant is glycerol.

6. The dentifrice composition of claim 2, wherein the coloring agent is in amount from 0.01% to 5% by weight, based on the weight of the composition.

7. The dentifrice composition of claim 1, further comprising additional agents selected from fluoride salts, one or more of an abrasive, a surfactant, an enzyme, a thickener, an antimicrobial agent, a flavoring agent, and a combination of two or more thereof.

8. The dentifrice composition of claim 1, wherein the composition is a toothpaste, a paste, a gel, and may be in form of a deep striped, a surface striped, a multilayered, having the gel surrounding the paste, or any combination thereof.

* * * * *